(12) United States Patent
Patel et al.

(10) Patent No.: US 8,360,974 B2
(45) Date of Patent: Jan. 29, 2013

(54) DIAGNOSTIC METHOD FOR HIGH SENSITIVITY DETECTION OF COMPONENT CONCENTRATIONS IN HUMAN GAS EMISSIONS

(75) Inventors: C. Kumar N. Patel, Los Angeles, CA (US); L. Ravi Narasimhan, Los Angeles, CA (US)

(73) Assignee: Pranalytica, Inc., Santa Monica, CA (US)

( * ) Notice: Subject to any disclaimer, the term of this patent is extended or adjusted under 35 U.S.C. 154(b) by 1741 days.

(21) Appl. No.: 11/351,574

(22) Filed: Feb. 9, 2006

(65) Prior Publication Data

US 2006/0217626 A1   Sep. 28, 2006

Related U.S. Application Data

(62) Division of application No. 09/812,067, filed on Mar. 19, 2001, now Pat. No. 7,004,909.

(51) Int. Cl.
*A61B 5/00* (2006.01)

(52) U.S. Cl. ........ 600/300; 600/562; 600/532; 250/343; 356/300; 356/432

(58) Field of Classification Search ........... 600/529–543
See application file for complete search history.

(56) References Cited

U.S. PATENT DOCUMENTS

| | | | |
|---|---|---|---|
| 3,649,199 A * | 3/1972 | Littlejohn | 436/178 |
| 3,792,272 A | 2/1974 | Harte et al. | |
| 3,820,901 A | 6/1974 | Kreuzer | |
| 3,853,503 A | 12/1974 | Folmer, Jr. | |
| 3,893,771 A | 7/1975 | Bell | |
| 4,041,313 A | 8/1977 | Potter et al. | |
| 4,273,450 A * | 6/1981 | Watanabe et al. | 356/433 |
| 4,303,343 A | 12/1981 | Patel et al. | |
| 4,310,762 A | 1/1982 | Harris et al. | |
| 4,314,564 A | 2/1982 | Albarda | |
| 4,471,220 A * | 9/1984 | Perry et al. | 250/339.04 |
| 5,121,337 A * | 6/1992 | Brown | 702/28 |
| 5,284,054 A | 2/1994 | Loebach | |
| 5,543,621 A | 8/1996 | Sauke et al. | |
| 5,640,014 A | 6/1997 | Sauke et al. | |
| 5,747,809 A | 5/1998 | Eckstrom | |
| 5,813,767 A * | 9/1998 | Calabro' et al. | 374/142 |
| 5,834,632 A | 11/1998 | Olender et al. | |
| 5,864,398 A | 1/1999 | Murnick | |
| 5,945,592 A | 8/1999 | Chou | |

(Continued)

OTHER PUBLICATIONS

LB. Kreuzer and C.K.N. Patel, Nitric Oxide Air Pollution: Detection by Optoacoustic Spectroscopy, Science 173(3991):47-49 (1971).

(Continued)

*Primary Examiner* — Navin Natnithithadha
*Assistant Examiner* — Karen Toth
(74) *Attorney, Agent, or Firm* — Jones Day

(57) ABSTRACT

A method for detecting component concentrations in human gas emissions such as breath and gas emitted from skin. A gas sample containing a specified component is collected into a gas cell using a pump and a series of valves to draw the gas sample into the cell and control the gas pressure within the cell. A tunable optical radiation beam is passed through the gas cell and the amount of energy absorbed by the specified component may be measured indirectly by taking the difference between the incident and emerging beam energy or directly by optoacoustic methods. Concentrations of the specified component as small as 0.1 ppB may be determined. Additionally, the tunable optical radiation beam may be multiplexed for use with a plurality of systems utilizing the beam for medical purposes.

17 Claims, 9 Drawing Sheets

U.S. PATENT DOCUMENTS

| | | | |
|---|---|---|---|
| 5,961,470 | A | 10/1999 | Wagner et al. |
| 6,010,459 | A * | 1/2000 | Silkoff et al. ............... 600/532 |
| 6,248,078 | B1 | 6/2001 | Risby et al. |
| 6,327,896 | B1 | 12/2001 | Veronesi et al. |
| 6,363,772 | B1 * | 4/2002 | Berry ..................... 73/24.02 |
| 6,594,016 | B1 * | 7/2003 | Te Lintel Hekkert et al. ............... 356/437 |
| 6,865,408 | B1 * | 3/2005 | Abbink et al. ............... 600/310 |
| 2011/0032516 | A1 * | 2/2011 | Zhou et al. ............... 356/73 |
| 2011/0164248 | A1 * | 7/2011 | Bushaw et al. ............... 356/318 |
| 2011/0188046 | A1 * | 8/2011 | Sanders et al. ............... 356/451 |
| 2012/0002212 | A1 * | 1/2012 | Chandler et al. ............... 356/454 |

OTHER PUBLICATIONS

L.B. Kreuzer, N.D. Kenyon, and C.K.N. Patel, Air Pollution: Sensitive Detection of Ten Pollutant Gases by Carbon Monoxide and Carbon Dioxide Lasers, Science 177(4046): 347-49 (1972).

C.K.N. Patel and R.J. Kerl, A new optoacoustic cell with improved performance, Appl. Physics Letters 30(11):578-79 (1977).

C.K.N. Patel, Laser Detection of Pollution, Science 202(4364): 157-173 (1978).

R.J. Brewer and C.W. Bruce, Photoacoustic spectroscopy of $NH_3$ at the 9-$\mu$m and 10-$\mu m$ $^{12}C^{16}O_2$ laser wavelengths, Appl. Optics 17(23): 3746-49 (1978).

H. Sauren, D. Bicanic, H. Jalink, and J. Reuss, High-sensitivity, interference-free, Stark-tuned $CO_2$ laser photoacoustic sensing of urban ammonia, J. Appl. Physics 66(10): 5085-87 (1989).

S. Davies, P. Spanel, and D. Smith, Quantatative analysis of ammonia on the breath of patients in end-stage renal failure, Kidney Int'l 52: 223-28 (1997).

P. Murtz, L. Menzel, W. Bloch, A. Hess, O. Michel, and W. Urban, LMR spectroscopy: a new sensitive method for on-line recording of nitric oxide in breath, J. Appl. Physiol. 86(3): 1075-1080 (1999).

D. Smith, P. Spanel, and S. Davies, Trace gases in breath of healthy volunteers when fasting and after a protein-calorie meal: a preliminary study, J. Appl. Physiol. 87(5): 1584-88 (1999).

* cited by examiner

| LASER AT FREQUENCY $f_1$ | | | |
|---|---|---|---|
| | OPTOACOUSTIC SIGNAL (milliVolts) | LASER POWER P (Watts) | NORMALIZED SIGNAL (milliVolts/Watts) |
| INTIAL ROOM AIR SIGNAL | 0.732 to 0.735 | 2.13 | 0.35 |
| 2 MINUTE SKIN SIGNAL | 0.777 to 0.801 | 2.13 | 0.37 |
| ROOM AIR SIGNAL AFTER 5 MINUTES | 0.745 to 0.760 | 2.13 | 0.353 |
| | | | |
| NET SKIN SIGNAL | | | 0.017 TO 0.02 |

FIG. 12A

| LASER AT FREQUENCY $f_2$ | | | |
|---|---|---|---|
| | OPTOACOUSTIC SIGNAL (milliVolts) | LASER POWER P (Watts) | NORMALIZED SIGNAL (milliVolts/Watts) |
| INTIAL ROOM AIR SIGNAL | 0.626 to 0.65 | 2.25 | 0.284 |
| 2 MINUTE SKIN SIGNAL | 0.645 to 0.666 | 2.25 | 0.29 |
| ROOM AIR SIGNAL AFTER 5 MINUTES | 0.638 to 0.666 | 2.25 | 0.29 |
| | | | |
| NET SKIN SIGNAL | | | 0.001 TO 0.006 |

FIG. 12B

DIAGNOSTIC METHOD FOR HIGH SENSITIVITY DETECTION OF COMPONENT CONCENTRATIONS IN HUMAN GAS EMISSIONS

RELATED APPLICATIONS

This application is a divisional of U.S. patent application Ser. No. 09/812,067, filed Mar. 19, 2001 now U.S. Pat. No. 7,004,909.

BACKGROUND OF THE INVENTION

The field of this invention relates to absorption spectroscopy, more specifically, it pertains to medical uses of absorption spectroscopy to quantify component concentrations in human gas emissions, such as breath and gas emitted through the skin.

Dialysis Population

It is estimated that in the United States, approximately 246,000 patients underwent kidney dialysis treatment in 1999, "Living ESRD Patients on December 31," Table D.1, United States Renal Data System (USRDS), 2000 ADR/Reference Tables, Section D—Treatment Modalities, www.usrds.org. Most of these patients undergo the treatment in clinics, hospitals, or specialized dialysis centers. However, a sizable number of the patients are able to avail themselves of dialysis through peritoneal dialysis treatments at home, Id. The typical kidney dialysis station costs approximately $25,000. For an effective deployment of such an investment, it is necessary to treat patients as efficiently as possible. It has been observed that ammonia concentration in exhaled human breath of a dialysis patient undergoing hemodialysis drops from over 10,000 ppB (parts per billion) to just over 1,000 ppB during the dialysis. Davies et al., "Quantitative Analysis of Ammonia on the Breath of Patients in End-Stage Renal Failure," Kidney International 52:223-228 (1997). Physicians often use the smell of a patient's breath as one indicator of health and well-being. For detecting ammonia, this technique is not very sensitive, as is seen from the fact that the lower limit of human perception for the presence of ammonia through smell is approximately 53 ppm (parts per million), Merck Index, 10$^{th}$ ed., p. 74. Accordingly, the physical examination of a patient by a physician employing simply smelling of patient breath to gather information regarding the status of patient kidney function is impractical, save for the most severe cases.

On the basis of the above discussion, a reliable and quantitative measurement of ammonia concentration in breath would be an excellent diagnostic tool for ascertaining incipient kidney trouble, the need for immediate dialysis treatment, determining the efficacy of the procedure during dialysis, and detecting the end-point of dialysis treatment. Determining the scheduling of dialysis treatment through actual measurements of ammonia concentrations in breath would be far superior to providing dialysis at fixed and predetermined intervals and durations. One of the key factors in favor of end-point detection of dialysis treatment is that the patient would not have to remain subjected to the dialysis procedure for any time longer than necessary. From the patient's viewpoint, less time spent connected to a dialysis apparatus equates to reduced physical and perhaps emotional discomfort. From the physician's viewpoint, reliable, accurate, real-time information on the progress of treatments equates to an improved ability to respond to a patient's changing treatment needs. From the viewpoint of the dialysis treatment providers, providing dialysis when called for through an accurate determination of the need for dialysis, and for only the necessary length of time, would allow for more efficient usage of the dialysis facilities and associated medical personnel. Thus, there has long been a need for accurate end-point detection during the dialysis procedure. Quantitative determination of ammonia levels in breath offers a fast, painless solution at a reasonable cost.

Turning now from the situation in a dialysis facility to the home dialysis section of the market, USRDS data indicates that at present approximately $265 million associated with home dialysis were covered by Medicare payments, "Medicare Payments for ESRD Patients," Table K.1, USRDS 2000 ADR/Reference Tables, Section K—Economic Costs of ESRD, www.usrds.org. For these home health care patients, the ability to non-invasively monitor their kidney health status by measurement of breath ammonia would provide two significant benefits. The first is that the individual could undergo his or her treatment when indicated by elevated levels of breath ammonia, a surrogate for elevated blood urea nitrogen. The second benefit is that the measurements of breath ammonia made during the dialysis treatment would provide an accurate end-point for the treatment. Such in-home dialysis patients could obtain the benefits of such technology in the absence of a trained health care professional.

The total Medicare payments for ESRD patients in 1998 amounted to approximately $11 billion, "Medicare Payments for ESRD Patients," Table K.1, USRDS 2000 ADR/Reference Tables, Section K—Economic Costs of ESRD, www.usrds.org. A large fraction of these costs are attributable to present treatment methods which rely on regularly scheduled treatments for prescribed lengths of time. Changing to a treatment protocol based on objective measures of treatment efficacy and efficiency will have a major impact on a very large and growing cost base. In addition to being an indicator for the need for dialysis treatment, the presence of ammonia in a patient's breath is also expected to be an indicator of liver transplant success, kidney and liver function in premature babies, and an indicator for preeclempsia in women during late stage pregnancies.

Asthmatic Population

The number of asthmatic individuals in the United States has been estimated between 14.6 million and 17.2 million patients, "Vital and Health Statistics," Current Estimates From the National Health Interview Survey, 1994 (Series 10: Data for the National Health Survey No. 193, DHHS Publication No. 96-1521), p. 94. Of these, approximately 10.4 million patients are classified as suffering from chronic asthma. The 1987 National Medical Expenditure Survey results, adjusted to 1996 dollars, show that the direct medical costs associated with asthma patients, including direct hospital outpatient services, hospital inpatient stays, emergency department visits, physician and facility payments and prescribed medicines are in excess of $5 billion, Smith et al., "A National Estimate of Economic Costs of Asthma," Am. J. Respir. Crit. Care Med. 156, 787-793 (1997).

There has been a long felt need for technology sufficient to allow for the advance warning of an impending asthma episode which would permit a patient either to immediately begin medication or to seek medical intervention. A surrogate for an indication of asthma treatment is the presence of nitric oxide in the human breath. However, an instrument capable of providing such warning would require the capability of measuring levels of nitric oxide of about 100 ppB with a resolution of less than about 10 ppB. Such an instrument must further detect these low levels of nitric oxide in the presence of other constituents of human breath such as water vapor and carbon dioxide. In addition, any such instrument should be simple to use, maintain, and calibrate, thus making it useable in hospital or in home health care settings.

Using Lasers to Measure Component Concentrations in a Gas Sample

Spectroscopy has been used to determine the concentration of a component gas in a given sample for many years. Initially, spectroscopy was conducted using an infrared lamp as an energy source, and passing the light through a sample. The absorption, and thus the concentration of a component within the sample, is measured by normalizing the light energy remaining after passing through the sample with the light energy that entered the sample. Unfortunately, because of the difficulty in controlling the output of the source, and the need to have the light travel as great a distance as possible within a sample to maximize absorption, this process is incapable of easily measuring the concentration of trace components making up less than 1 ppm of a gas sample within a short time interval. See, for example, U.S. Pat. No. 3,792,272.

Over the last thirty years techniques have been developed that allow the measurement of component concentrations within a gas sample. One method, described in "Spin Flip Raman Laser and Infrared Spectroscopy," *Phys. Rev. Lett.* 25:8-11 (1970), incorporated herein by reference, passes a laser beam from a tunable radiation source, the beam frequency corresponding to a fundamental absorption peak frequency (also known in the art as a vibrational-rotational peak frequency) of the component being measured, through a test sample to obtain the trace component concentration. The measurement is typically made by first splitting the beam into two parts, a first beam and a second beam, using a beam splitter having known beam splitting properties. The first beam is directed to a first detector where its power is measured. The power of the first beam is used in conjunction with the known properties of the beam splitter to determine the power of the second beam incident on the test sample. The second beam is passed through the test sample, where it is partially absorbed by the component in the test sample, resulting in an attenuation of the second beam's total energy. Upon emerging from the test sample, the energy of the second beam is measured by a second detector. The output of the second detector, therefore, contains the natural variations and fluctuations of the power of the laser beam diminished slightly due to attenuation from absorption in the test sample. The energy absorbed by the component in the test sample is derived from the difference between the output of the first and second detectors. The component concentration within the test sample is obtained by comparing the above absorption measurement with the absorption measurement obtained from a sample having a known component concentration.

The sensitivity afforded by this technique is, however, limited. When measuring small absorption amounts, i.e., the test sample has only trace amounts of the gas being measured, the power of the beam, both incident upon and emerging from the test sample, is very large in comparison to the amount of energy absorbed by the trace component. Therefore, the error margins present in the power measurements will have a larger effect on the calculation of the relatively small absorption amount. By way of example, this technique may be likened to determining the weight of the captain of an oil super tanker by weighing the tanker with and without the captain on the ship and subtracting the latter measurement from the former.

The sensitivity of the preceding technique may be enhanced by placing test sample and the laser within an optical cavity. The optical cavity is formed by two very highly reflective mirrors, each having a reflectivity of approximately between 99.95% and 99.99%. Within the optical cavity, the optical power passing through the test sample at any given time is greatly increased due to the beam reflecting back and forth between the mirrored surfaces. A small but measurable amount of energy from the beam passes through the mirror as "leakage". This leakage is used to accurately determine the amount of energy circulating in the cavity according to well known principles in the art. To determine the absorption, and therefore the concentration, of a component within a test sample using an optical cavity, the leakage from the cavity in the absence of the test sample is measured, yielding the energy of the beam incident on the test sample, and subtracting from that the leakage measured in the presence of the test sample. However, even with the use of the optical cavity, this technique is limited because it measures absorption indirectly by taking the difference between the laser energy before it enters the sample and the laser energy after it passes through the sample.

Calorimetric Detection:

A second method, described in "Nitric Oxide Air Pollution: Detection by Optoacoustic Spectroscopy," *Science* 173:45-47 (1971), incorporated herein by reference, greatly increases the sensitivity of absorption measurements through the use of single-pass optoacoustic spectroscopy. In this method, an acoustic microphone is placed in a gas cell containing a test sample having an unknown concentration of a component gas. A pulsed or chopped tunable laser beam is passed through the gas cell and the energy absorbed by the component gas is directly measured using the acoustic microphone. If the test sample contains non-absorbing gases or the frequency of the beam does not correspond to a fundamental absorption peak of any gas within the test sample, including the component gas, the beam exits the gas cell unattenuated. However, if the test sample contains a component gas that is absorbing and the beam frequency corresponds to a fundamental absorption peak frequency of the component gas, energy from the beam is absorbed by the component gas. This energy absorption causes slight heating within the test sample that occurs at regular and periodic intervals because the beam is pulsed and no absorption or heating occurs between pulses. The periodic heating of the test sample causes pressure fluctuations to be generated and propagated within the gas cell. These pressure fluctuations are sound waves and are detected by the microphone within the gas cell. The concentration of the component gas is determined by normalizing the acoustic energy, as measured by the microphone, with the energy of the beam incident on the gas cell, and comparing the result with a similar measurement using a sample having a known component concentration. This method provides a direct measurement of energy absorption in the cell, allowing the measurement of component concentrations making up as little as 1 ppB of the test sample.

The sensitivity of optoacoustic spectroscopy may be further enhanced by placing the gas cell containing the test sample in an optical cavity such as the one previously described. The pulsed beam is directed into the optical cavity in the manner previously described, and if the test sample contains a component gas that is absorbing and the beam frequency corresponds to a fundamental absorption peak frequency of the component gas, then the component gas absorbs energy from the beam. As in the previous method, the microphone is used to measure the acoustic energy. The energy of the beam incident on the gas cell is determined by measuring the leakage from the cavity in the absence of the test sample. The concentration of the component gas may then be obtained in the manner previously described. This variation of optoacoustic spectroscopy allows the detection of trace components that make up as little as 0.1 ppB (or 100 parts per trillion) of the test sample.

The high sensitivity spectroscopy methods described above, however, have been used chiefly for studying contaminant concentrations in the atmosphere and have found few applications in other fields.

Measuring Component Concentrations in Human Breath

Up until the last few years, one of the only applications of spectroscopy as applied to measuring the component concentration of human breath has been testing for ethyl alcohol, as described in U.S. Pat. No. 3,792,272. This application has found practically universal use by law enforcement agencies everywhere, but other uses and users are virtually non-existent. The technique disclosed in U.S. Pat. No. 3,792,272 passes frequency-modulated radiation in the infrared range, either from a laser or a collimated lamp, through a sample in order to determine the blood-alcohol content of an individual by measuring ethyl alcohol in the individual's breath. An individual being tested breathes into a heated collection chamber which keeps the breath from condensing and allows for a more accurate measurement. The collection chamber also contains two mirrors to reflect the light source back and forth and provide it with a longer path length in the collection chamber. The amount of radiation energy exiting the collection chamber is measured and then normalized using the radiation energy that entered the collection chamber, yielding the amount of energy absorbed by the ethyl alcohol in the sample. However, for the same reasons previously described, this method is not capable of detecting minute component concentrations within a breath sample.

U.S. Pat. No. 4,314,564 discloses improvements to the alcohol breath test described above. These improvements, however, relate only to eliminating the need to heat the collection chamber. This improved device eliminates the need to heat the chamber by accounting for the relative humidity within the gas chamber and the ambient atmospheric humidity. However, in all other regards, the improved alcohol breath test is the same as the previous one and is incapable of measuring minute component concentrations.

More recently, human breath has been examined for the presence of isotopes or isotopically labeled molecules, as disclosed in U.S. Pat. Nos. 5,543,621 and 5,961,470, respectively. Both of these human breath tests, however, are not capable of detecting trace component concentrations in exhaled human breath because they rely on the same general techniques discussed used in the detection of alcohol. Additionally, U.S. Pat. No. 5,543,621 only measures the ratio of the concentration of the isotopically substituted component to the concentration of the more common form of the element; it does not independently measure the actual concentration of the isotope.

Another recent use of spectroscopy to measure gaseous components of human breath utilizes complex mathematical approximation methods to arrive at the concentration of the gaseous components, such as is disclosed in U.S. Pat. No. 5,807,750. This method passes multi-spectral collimated light through a gas sample and detects the power of the emerging light using an array of detectors, with each detector in the array set to detect the emerging light at a single frequency. The signal obtained from the detector array is passed to a computer system which performs the complex mathematical calculations to arrive at the concentration of the component gases. The complex mathematical calculations are based on experimentally derived algorithms for several species of gases, including the component of interest being measured and many possible interfering species. The experimentally derived algorithms form a matrix which the computer system uses in an iterative process to determine, from the output of the detector array, a component absorption approximation free of absorption from interfering species. The absorption approximation is thereafter used to determine the concentration of the component of interest. This method, however, may not be ideal for use under all circumstances because the complex mathematical analysis requires the presence of a computer capable of performing such analysis and the creation of experimentally derived algorithms for each component measured and all possible interfering species.

SUMMARY OF THE INVENTION

The present invention provides a diagnostic method and apparatus for high sensitivity detection of trace component concentrations in human gas emissions such as exhaled breath and gas emitted through the skin. Trace concentrations of gases such as, for example, nitrogen oxides, ammonia, carbon dioxide, and chemical groups such as alcohols, ketones, and alkanes, may be detected and quantified. A sample of the human gas emissions which may contain the specified component is first collected into a gas cell. Where the human gas emissions comprise expired human breath, the expired breath is drawn through a conduit and into the gas cell by a vacuum pump. Where the human gas emissions comprise gas emitted through the skin, the gas is trapped and drawn through a conduit and into the gas cell by a vacuum pump. The vacuum pump and one or more valves may be utilized to control the gas pressure within the gas cell.

In a first separate aspect of the invention, human breath, suspected of comprising a specified component, is collected into the gas cell. The gas cell is placed in an optical cavity and a tunable optical radiation beam, i.e., a laser, is passed through the gas cell at two frequencies, each at a distinct and different time. The first frequency corresponds to a fundamental absorption peak frequency of the component and the second frequency does not correspond to a fundamental absorption peak frequency of the specified component. For each beam frequency, the energy of the beam emerging from the gas cell is measured when the gas cell (1) contains a reference sample, (2) does not contain the specified component, and (3) contains the gas emissions. The concentration of the specified component may be determined from the measurements.

In a second separate aspect of the invention, human breath, suspected of comprising a specified component, is collected into the gas cell. The gas cell may or may not be placed within an optical cavity. A pulsed tunable optical radiation beam is passed through the gas cell at two frequencies, each at a distinct and different time, with the first frequency corresponding to a fundamental absorption peak frequency of the specified component and the second frequency not corresponding to a fundamental absorption peak frequency of the specified component. When the pulsed beam passes through the gas cell at the first frequency, the specified component partially absorbs the pulsed beam and generates and optoacoustic signal. A microphone is placed in the gas cell to detect and measure the optoacoustic signal, the amplitude of which corresponds to the amount of energy absorbed by the specified component. When the pulsed beam passes through the gas cell at the second frequency, the specified component does not absorb the pulsed beam. Therefore, any measured optoacoustic signal at the second frequency is from absorption by unknown sources and thus background signal. The power of the beam emerging from the gas cell is also measured for each frequency. The concentration of the specified component may be determined from the obtained measurements.

In a third separate aspect of the invention, human breath, suspected of comprising a specified component, is collected into the gas cell. The gas cell may or may not be placed within an optical cavity. A small modulation frequency is superimposed on the frequency of the tunable optical radiation beam. As the beam is passed through the gas cell, the beam frequency is swept through a range of frequencies, with at least one fundamental absorption peak frequency of the specified component included in the range of frequencies. The power of the beam emerging from the gas cell is measured. The beam is also monitored at the modulation frequency, and the amplitude of the beam at the modulation frequency is measured. The concentration of the specified component may be determined from the obtained measurements.

In a fourth separate aspect of the invention, human breath, suspected of comprising a specified component, is collected into the gas cell. A pulsed optical radiation beam from a discretely tunable laser is passed through the gas cell at two different discrete frequencies of the laser. The first discrete frequency is near a fundamental absorption peak frequency of the specified component. The second discrete frequency is not near a fundamental absorption peak frequency of the specified component. The gas pressure in the gas cell is increased to broaden the fundamental absorption peak of the specified component so that the absorption peak encompasses the first discrete frequency. A microphone is placed in the gas cell to detect the optoacoustic signal resulting from absorption of the pulsed beam. At the first discrete frequency, the optoacoustic signal in the gas cell is generated by absorption from the specified component and any additional absorbing materials that are present. At the second discrete frequency, the optoacoustic signal in the gas cell is generated by only the additional absorbing materials. The energy absorbed by the specified component is the difference between the optoacoustic signal generated at first frequency and the optoacoustic signal generated at the second frequency.

In a fifth separate aspect of the invention, human breath, suspected of comprising a specified component, is collected into the gas cell. A pulsed optical radiation beam from a discretely tunable laser is passed through the gas cell at three different discrete frequencies of the laser. The first and third discrete frequencies are near different fundamental absorption peak frequencies of the specified component. The second discrete frequency is not near a fundamental absorption peak frequency of the specified component. The gas pressure in the gas cell is increased to broaden the fundamental absorption peak of the specified component so that the absorption peaks encompasses the first and third discrete frequencies. A microphone is placed in the gas cell to detect the optoacoustic signal resulting from absorption of the pulsed beam. At the first and third discrete frequencies, the optoacoustic signals in the gas cell are generated by absorption from the specified component and any additional absorbing materials that are present. At the second discrete frequency, the optoacoustic signal in the gas cell is generated by only the additional absorbing materials. The energy absorbed by the specified component, and thus the concentration, is the difference between the optoacoustic signal generated at first frequency and the optoacoustic signal generated at the second frequency. The concentration measurement is verified by also determining the concentration of the specified component using the measured signals at the third frequency and the second frequency. The verification ensures that the absorption measurement is not interfered with by absorption from other unknown sources present in the breath sample.

In a sixth separate aspect of the invention, gas emitted through skin is collected by sealing a collection chamber against the skin and delivering through the collection chamber an inert gas to collect the emitted gas into a gas cell for analysis.

In a seventh separate aspect of the invention, gas emissions through skin are analyzed, using any of the methods described herein, for the presence and concentration of a specified component.

In an eighth separate aspect of the invention, a system may be employed whereby a single tunable optical radiation source may be simultaneously utilized by a plurality of medical systems.

In a ninth separate aspect of the invention, a system may be employed whereby a single tunable optical radiation source may be utilized by a plurality of medical systems in a sequential manner.

Other aspects, advances and novel features of the invention will become apparent from the following detailed description of the invention when considered in conjunction with the accompanying drawings.

BRIEF DESCRIPTION OF THE DRAWINGS

In the figures, wherein like numbers reflect similar elements:

FIGS. 12a and 12b are test results using the apparatus of FIG. 10;

DESCRIPTION OF THE PREFERRED EMBODIMENTS

Figure 1:
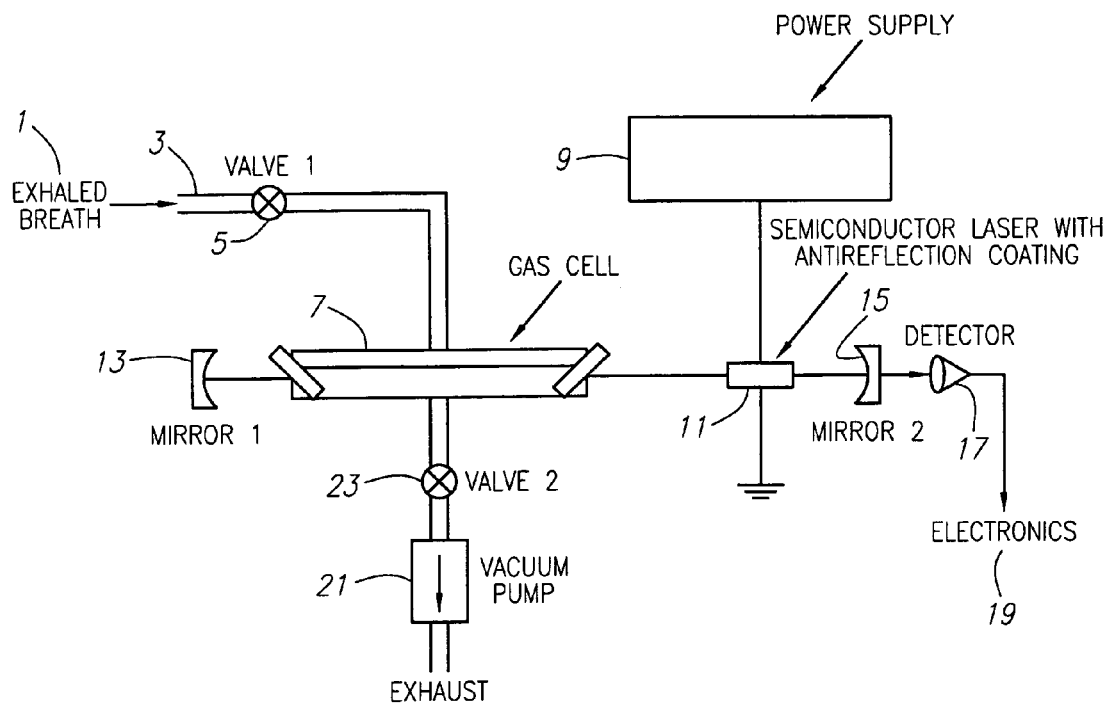
FIG. 1 illustrates an apparatus using a tunable optical radiation source to make intracavity absorption measurements of human breath.

In the embodiment of the invention illustrated in FIG. 1, a gas sample of exhaled breath 1 suspected of containing a specified component is drawn through a conduit 3 and a valve 5, and into a gas cell 7 by means of a vacuum pump 21. The gas pressure in the gas cell 7 may be adjusted by the relative openings of the valves 5, 23, with the gas pressure preferably being between 10 Torr and 500 Torr.

A power supply 9 powers a tunable laser 11, preferably a semiconductor laser with an operational output of at least 1 mW (milliwatt), having anti-reflection coatings and capable of operating near at least one fundamental absorption peak frequency of the specified component being measured. A laser with an output of at least 1 mW enables the concentration of the specified component to be measured within approximately 1 ppB in approximately ten seconds of operating time. The type of laser used may vary depending upon the particular needs of the user and includes but is not limited to the following: carbon dioxide laser, carbon monoxide laser, spin-flip Raman laser, lead salt diode laser, and quantum cascade semiconducting laser. In practice, any laser, which fulfills the requirements, as described herein may be used.

The laser 11 emits a beam at two frequencies, $f_1$ and $f_2$, each at a distinct and different time. The first frequency, $f_1$, corresponds to a fundamental absorption peak frequency of the specified component, such as nitric oxide (NO) or ammonia ($NH_3$), and the second frequency, $f_2$, does not correspond to a fundamental absorption peak frequency of the specified component. Measurements, detailed below, are taken at each frequency. The beam passes through the gas cell 7 containing the exhaled breath 1, and strikes a first mirror 13, which reflects the beam back towards the laser 11 and a second mirror 15. The laser 11 has an antireflective coating, such as is commonly known in the art, so that the beam is not reflected by the surfaces of the laser 11. The first and second mirrors 13, 15 are both highly reflective, having a reflectivity of greater than 99.95%, and more preferably greater than 99.99%, and thus form an optical cavity. Within the optical cavity, the optical power of the beam passing through the gas cell 7 at any given time is greatly increased due to the beam repeatedly reflecting back and forth between the mirrored surfaces with only a small amount of transmission occurring at each mirror 13, 15. The transmission, or leakage, at each mirror represents only a small, fractional amount of the power of the beam incident upon the gas cell within the optical cavity. Those skilled in the art will recognize that the leakage may be used to accurately determine the amount of energy circulating in the optical cavity, and thus the power of the beam incident on the gas cell.

At the first frequency, a portion of the beam power is absorbed by the specified component the leakage is attenuated by the amount of the absorption. At the second frequency, the beam is not absorbed by the specified component and the leakage is unattenuated. The leakage at each frequency is detected by the detector 17 and measured and recorded by appropriate electronic circuitry 19 as the signal outputs. The methods used for detecting the beam and measuring and recording the signal outputs are performed by techniques well known to those skilled in the art.

Figure 2:
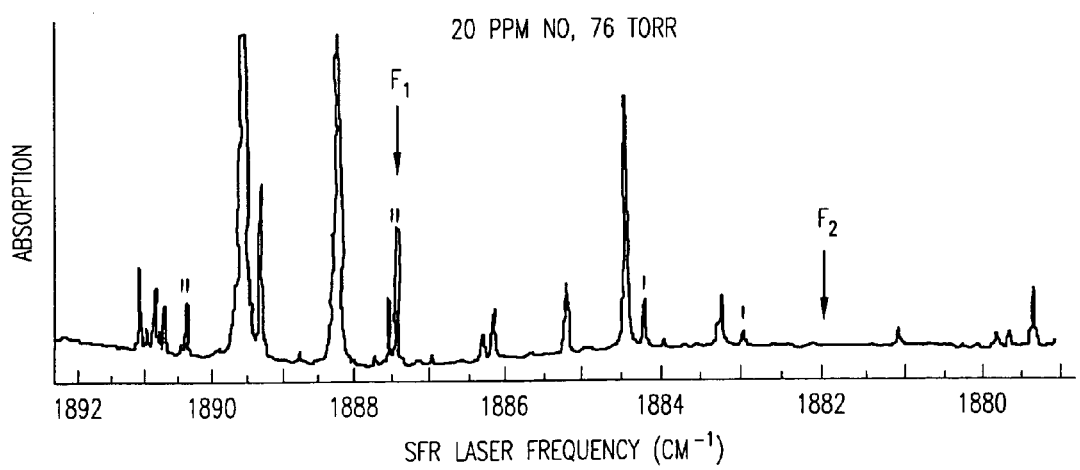
FIG. 2 illustrates the absorption spectrum for nitric oxide obtained using an optoacoustic spectrometer.

In connection with the absorption measurement of nitric oxide, a wavelength of approximately 5.2 μm may be used as the first frequency because this wavelength corresponds to a fundamental absorption peak frequency of nitric oxide. The laser 11 preferably has a power output of approximately 1 mW. FIG. 2 shows the measured absorption features of 20 ppM (parts per million) nitric oxide in nitrogen at a total pressure of 76 Torr as a function of laser frequency.

Concentration of the specified component, nitric oxide in the following example, is determined and proportioned as set out in the equation below and the accompanying description:

$$NO = constant1 * \frac{S_1(0) - S_1(NO)}{S_1(0)} * \frac{S_2(0)}{S_2(NO)}.$$

$S_1$ and $S_2$ are the signal outputs generated by the detector 17 when the laser 11 is operated at frequencies $f_1$ and $f_2$, respectively. $S_1(O)$ and $S_2(O)$ are the signal outputs generated by the detector 17 when there is an absence of nitric oxide in the gas cell 7. $S_1(NO)$ and $S_2(NO)$ are the signal outputs generated by the detector 17 when nitric oxide is present as a component of the gas in the gas cell 7. Constant1 in the preceding formula is determined by placing a reference sample having a known concentration of nitric oxide in the gas cell 7 and measuring the signal outputs as described above.

Figure 8:
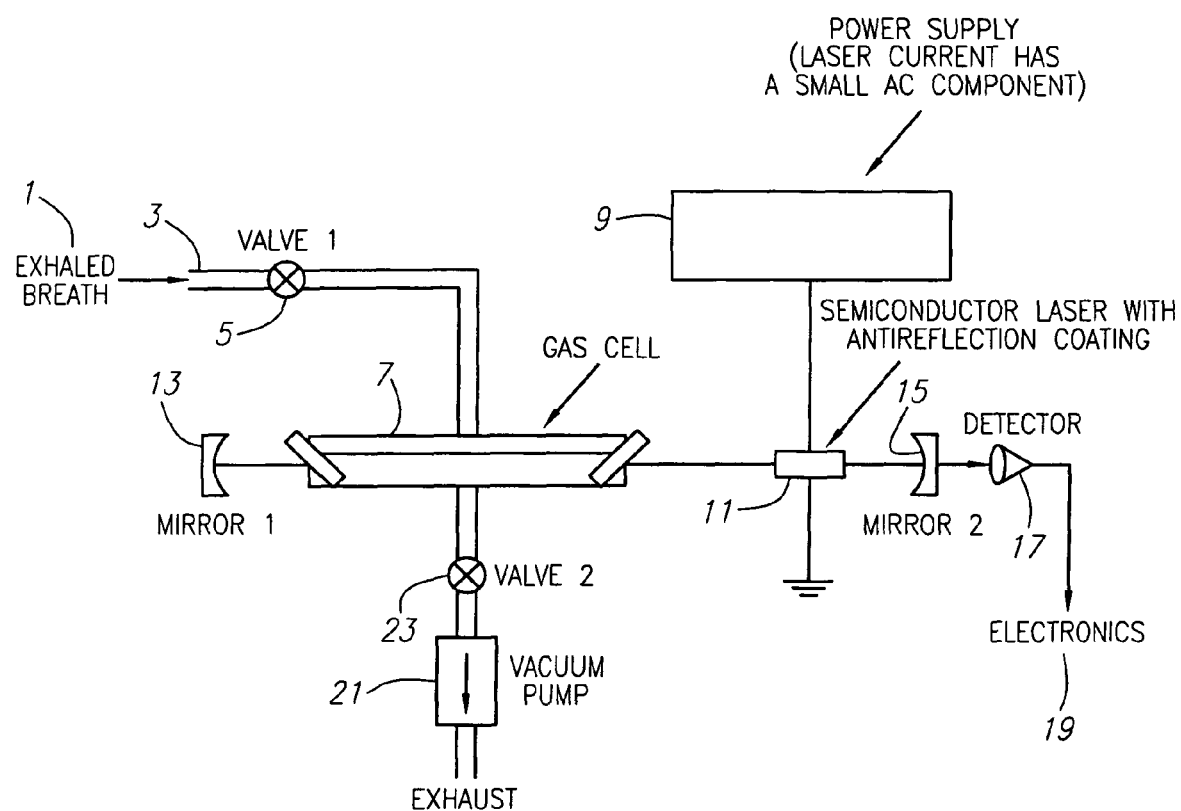
FIG. 8 illustrates an apparatus using frequency modulation spectroscopy to make absorption measurements of human breath.

FIG. 8 illustrates an alternative embodiment. The apparatus in FIG. 8 is the same as that illustrated in FIG. 1, however, in operation an AC modulation current is superimposed on the current output of the power supply 9. The modulation current causes an excursion in the beam frequency generated by the laser 11 because the beam frequency emitted by the laser 11 is dependent upon the supply current. The excursion of the beam frequency is preferably approximately 0.1% of the beam frequency, although other ratios of beam frequency to excursion are acceptable. The modulation current for power supply 9 should be adjusted to obtain the desired excursion amplitude. The frequency of the modulation current used preferably ranges between 1 kHz and 20 kHz, however frequencies outside this range may also be used. The beam frequency therefore comprises a modulation frequency, caused by the modulation current, superimposed on a base frequency. Thus, the beam frequency, $f_L$, emitted from the laser 11 is represented by:

$$f_L = f_0 + \Delta f * \sin(\omega t),$$

where $f_0$ is the base frequency of the beam in the absence of the modulation current, $\Delta f$ is the amplitude of the modulation frequency, and $\omega$ is the modulation frequency superimposed on the power supply 9.

Figure 6:
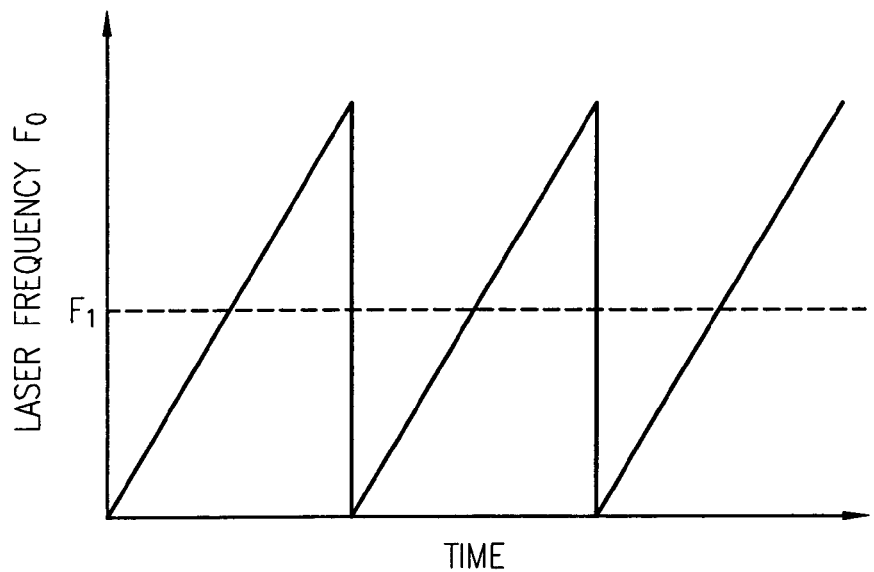
FIG. 6 illustrates a graph of time vs. laser frequency for the device of FIG. 5.
Figure 7:
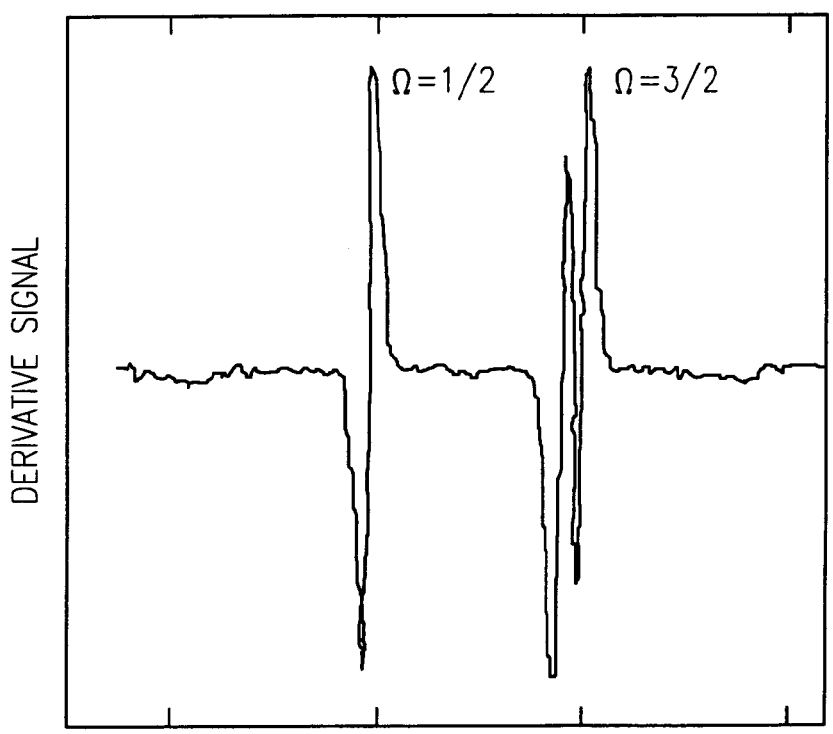
FIG. 7 illustrates a frequency modulated absorption signal obtained using the device of FIG. 5.

The base frequency, $f_0$, is continuously ramped, as is depicted graphically in FIG. 6, so that the beam frequency, $f_L$, sweeps through at least one fundamental absorption peak frequency, $f_1$ and passed through the gas cell 7. As the laser 11 sweeps through the fundamental absorption peak frequency, $f_1$, the absorption of the specified component varies at the same rate as the beam frequency. Those skilled in the art will recognize that the swing in the power of the beam emerging from the gas cell 7 at the modulation frequency is proportional to the slope of the absorption feature around the base frequency, i.e., proportional to the first derivative of the absorption with frequency. Therefore, if there is no absorption, the output of the signal at the modulation frequency is approximately zero. FIG. 7 illustrates the signal output of the beam emerging from a gas cell when measured at the modulation frequency, the gas cell containing nitrogen oxide as the specified component.

Figure 5:
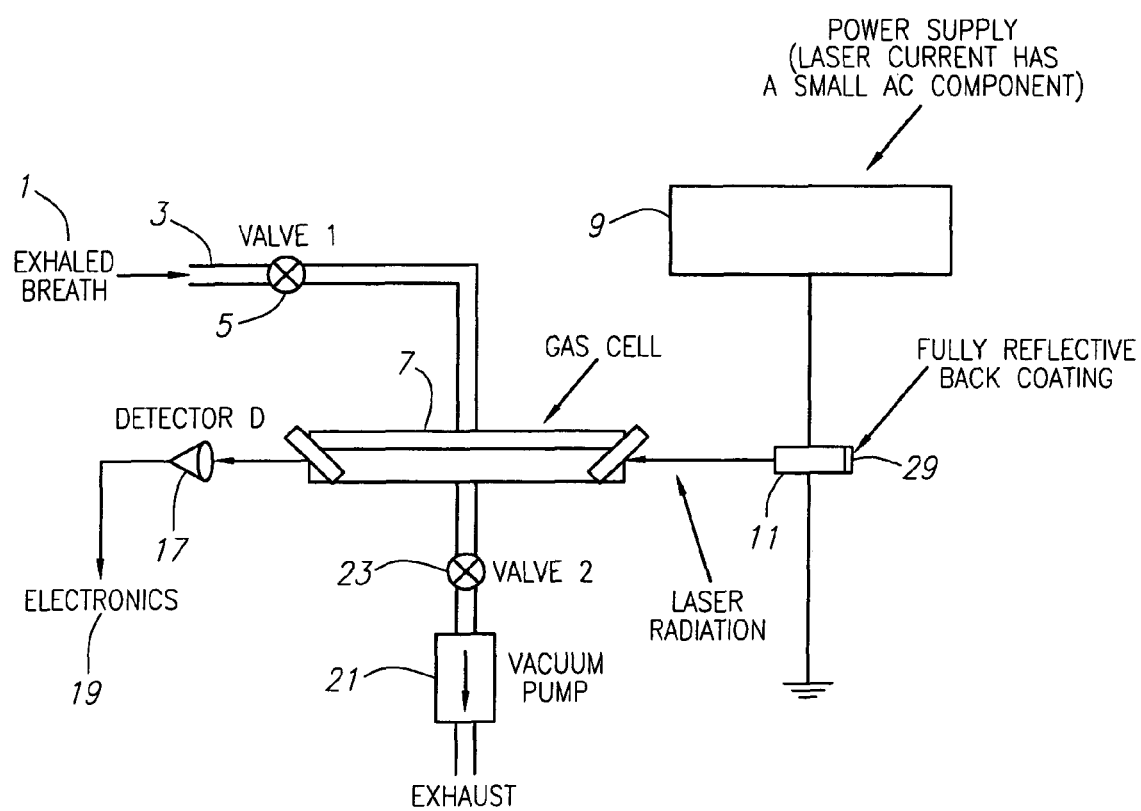
FIG. 5 illustrates an apparatus using a tunable optical radiation source to make frequency modulation absorption measurements of human breath.

To determine the absorption of the specified component, the electronic circuitry 19 monitors the beam and records as the first signal output the amplitude of the signal, $S_{AC}(f_1, \omega)$, at the modulation frequency, ω. Additionally, the detector 17 detects the beam emerging from the gas cell and the electronic circuitry 19 measures and records as the second signal output the power of the beam, $P(f_1)$. The concentration of the specified component is determined and proportioned as set out in the equation below and the accompanying description:

$$NO = \text{constant2} * \frac{S_{AC}(f_1, \omega)}{P(f_1)} = \text{constant2} * \frac{S_{AC}(f_2, \omega)}{P(f_2)},$$

where constant2 is again determined through using a reference sample with a known component concentration. A variation of this embodiment, depicted in FIG. 5, eliminates the use of the optical cavity and instead utilizes a laser 28 with a fully reflective back coating 29. The laser 11 directs the laser beam through the gas cell 7 and directly into the detector 17. The detector 17 is then used in conjunction with the electronic circuitry 19 to detect, measure, and record the signal outputs. The concentration of NO in the embodiment of FIG. 5 is determined in the same manner as described above for the embodiment depicted in FIG. 8.

Figure 3:
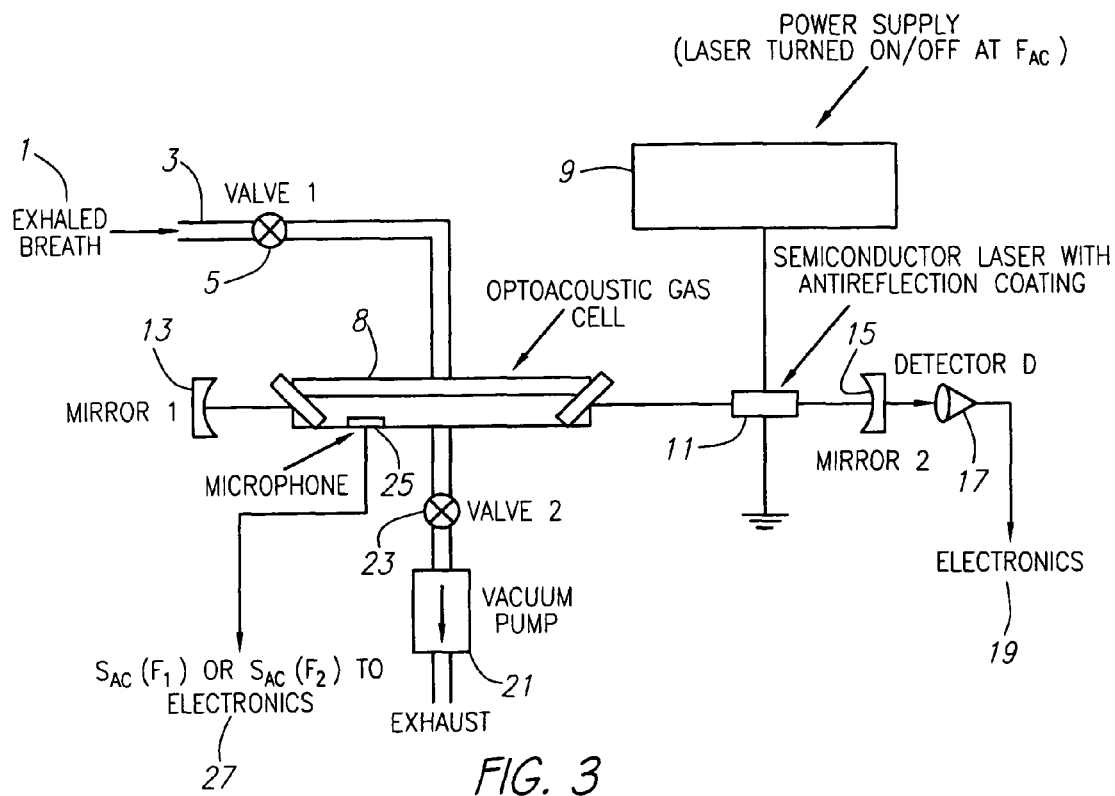
FIG. 3 illustrates an apparatus using a tunable optical radiation source to make optoacoustic absorption measurements of human breath.

FIG. 3 illustrates the preferred embodiment of the invention. In FIG. 3, a tunable laser emits a pulsed optical radiation beam. The beam is preferably pulsed in a regular and periodic manner at between 20 and 20,000 cycles per second. The pulsed beam is generated by modulating the power supply 9 between an on state and an off state at the desired pulse frequency. The laser 11 and the calorimetric gas cell 8 (also referred to as an optoacoustic gas cell by those skilled in the art) are placed in an optical cavity formed by a first mirror 13 and a second mirror 15. The pulsed beam is passed through the calorimetric gas cell 8 at two frequencies, each at a distinct and different time. The first frequency corresponds to a fundamental absorption peak frequency of the specified component and the second frequency does not correspond to a fundamental absorption peak frequency of the specified component. A microphone 25 is placed within the calorimetric gas cell 8 and connected to appropriate electronic circuitry 27 for measuring the signal output of the microphone 25. The apparatus of FIG. 3 may also be constructed with more than one microphone placed into the calorimetric gas cell 8 and connected to the electronic circuitry 25. The vacuum pump 21, the first valve 5, and the second valve 23 act in combination as previously described to draw a gas sample of exhaled breath 1 into the calorimetric gas cell 8, the exhaled breath 1 suspected of comprising a specified component.

When the beam passes through the calorimetric gas cell 8 at the first frequency, the specified component absorbs energy from the beam. This energy absorption causes slight heating within the exhaled breath 1 in the calorimetric gas cell 8. The heating occurs at regular and periodic intervals because the beam is pulsed and no absorption or heating occurs between pulses. The periodic heating of the exhaled breath 1 causes pressure fluctuations to be generated and propagated within the calorimetric gas cell 8. These pressure fluctuations are sound waves, known by those skilled in the art as optoacoustic signals, having a frequency that is approximately equal to the pulse frequency of the beam and an amplitude that is proportional to the absorption by the selected component. The microphone 25 detects the optoacoustic signals and generates a first signal output at the chopping frequency, $S_{AC}(f_1)$, that is measured and recorded by the electronic circuitry 27. As in the embodiment depicted in FIG. 1, a detector 17 detects the transmitted portion of the beam as the second signal output, which is measured and recorded by appropriate electronic circuitry 19.

When the beam passes through the calorimetric gas cell 8 at the second frequency, the specified component does not absorb energy from the beam. Therefore, no optoacoustic signal is should be present at the second frequency. However, if an optoacoustic signal is present at the second frequency, the signal is the result of absorption from unknown sources, such as contaminants in the gas or the gas cell itself, and is thus a measurement of background absorption. In circumstances where background absorption is measured, it should be subtracted from the optoacoustic signal measured at the first frequency to obtain the actual absorption by the specified component. The detector 17 detects and the electronic circuitry 19 measures and records the incident power of the beam at the second frequency.

Figure 4:
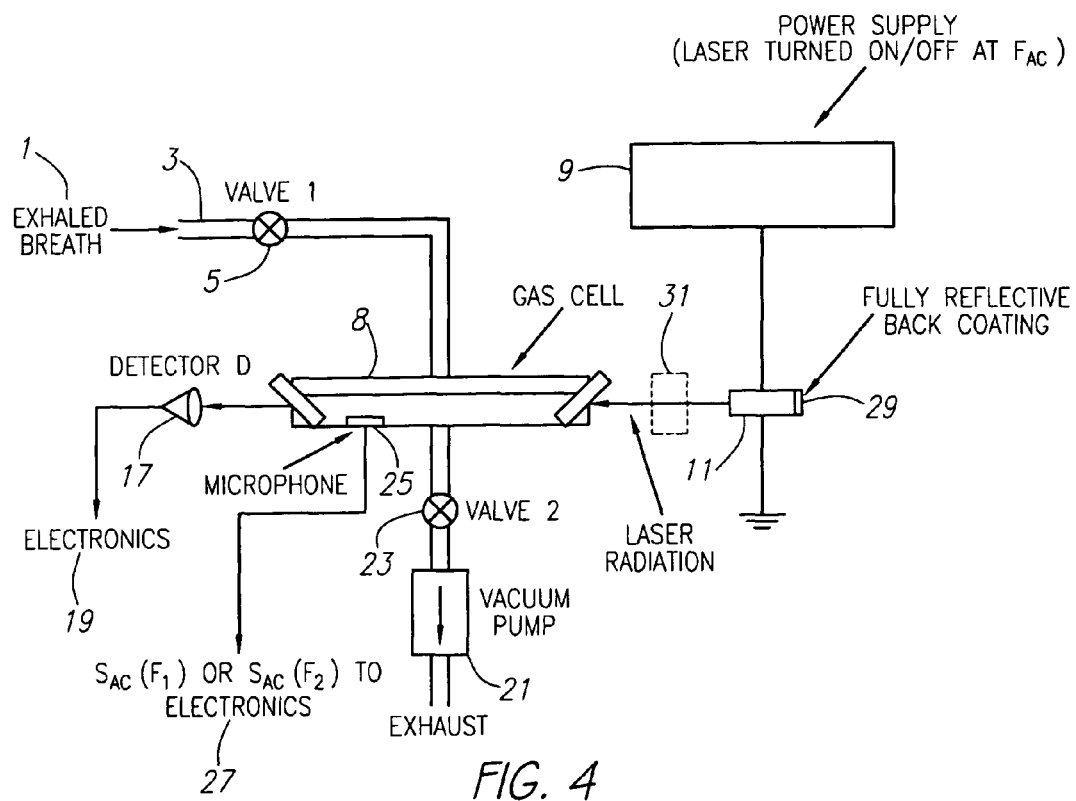
FIG. 4 illustrates an apparatus using a tunable optical radiation source to make optoacoustic absorption measurements of human breath.

In the absence of background absorption, concentration of the specified component in the exhaled breath 1, nitric oxide in the following example, is determined using the optoacoustic signal output and is proportioned as set out in the equation below and the accompanying description:

$$NO = \text{constant3} * \frac{S_{AC}(f_1)}{P(f_1)},$$

where $P(f_1)$ is the incident power of the laser 11 at $f_1$ as measured by the detector 17. As before, constant3 is determined by placing a reference sample with a known concentration of nitric oxide in the gas cell 7 and measuring the signal outputs as described above. A variation of this embodiment, depicted in FIG. 4, eliminates the optical cavity. Additionally, the pulsed beam may be generated by passing the beam emerging from the laser 11 through a chopper 31 in lieu of modulating the power supply 9. In this variation, the beam passes through the calorimetric gas cell 8 and directly into the detector 17. All other aspects of the embodiment depicted in FIG. 4 are the same as described for the embodiment depicted in FIG. 3.

Figure 9:
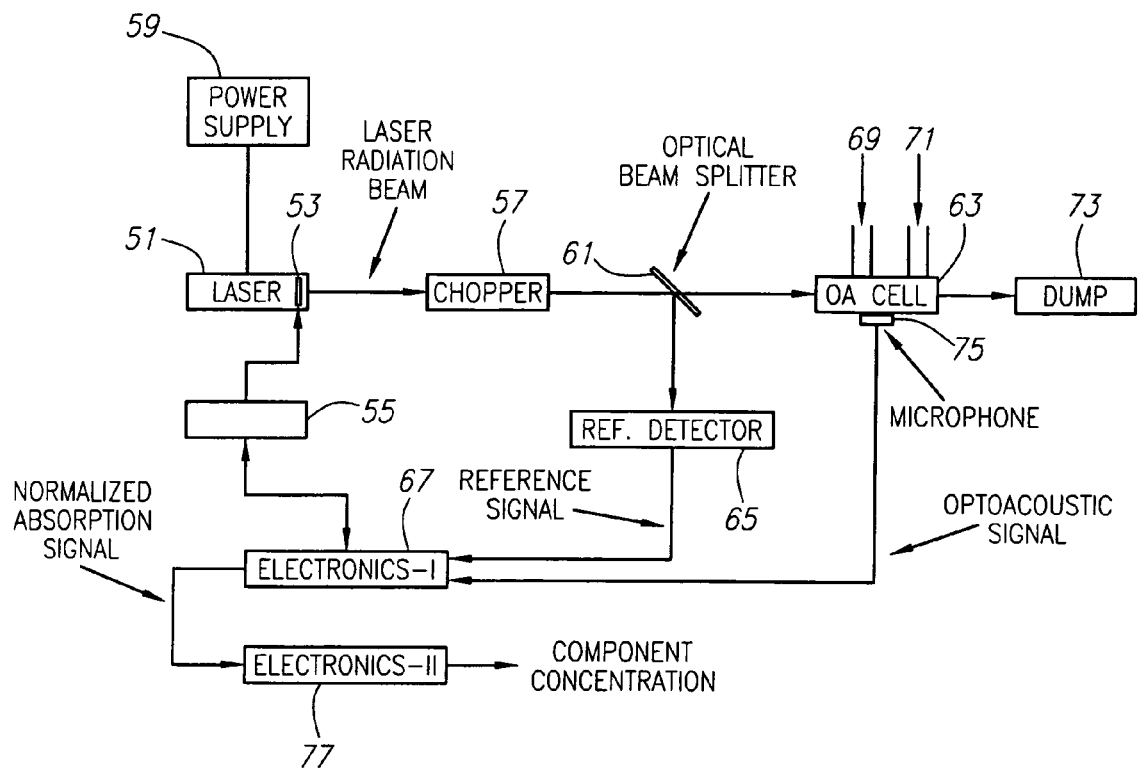
FIG. 9 illustrates an apparatus using a discretely tunable optical radiation source to make optoacoustic absorption measurements of human breath.

FIG. 9 illustrates an alternative embodiment utilizing a discretely tunable laser 51 such as, for example, a carbon dioxide laser or a carbon monoxide laser. Such lasers produce optical radiation beams having numerous discrete frequencies in the 9 µm to 11 µm and 4.5 µm to 7.5 µm region of the infrared spectrum. One of the discrete frequencies of the laser may be selected by reflecting or refracting the beam using an optical grating. Alternatively, as illustrated in FIG. 9, a grating or other wavelength selecting component 53 may be placed inside the optical cavity of the laser 51 and the wavelength selecting component 53 may be used (typically by tilting) to select a particular laser wavelength in a manner that is well known to those skilled in the art. In particular, the desired angle of the wavelength selecting component 53, and thus the particular beam frequency, is selected using the grating selector 55. A continuous beam, having a single discrete frequency, emerges from the laser 51 and passes through a chopper 57 to periodically interrupt the continuous beam and create a pulsed beam. Alternatively, the power supply 59 for the laser 51 may be modulated between an on state and an off state to create a pulsed beam.

The pulsed beam passes to a beam splitter 61 where the beam is divided into two separate beams, a first beam and a second beam. The first beam, preferably comprising approximately 95% of the total beam power, passes through the beam splitter 61 to the calorimetric gas cell 63. The second beam, preferably comprising approximately 5% of the total beam power, is deflected by the beam splitter 61 towards the reference detector 65. The reference detector 65 detects the power level of the second beam and the appropriate first electronic circuitry 67 measures and records the power of the second beam as a reference signal. The power of the first beam incident on the calorimetric gas cell 63 is determined using the reference signal and the known properties of the beam splitter 61. The relative power of the first beam and the second beam may be adjusted as needed by using a beam splitter having different known properties from the one used in FIG. 9. However, the second beam has a power that is preferably less than 10% of the pulsed beam's power.

The calorimetric gas cell 63 has a gas inlet 69 and a gas outlet 71 for drawing in a sample of human breath and controlling the gas pressure in the same manner described in conjunction with FIG. 1 using a conduit, valves, and a vacuum pump (not shown). The first beam passes into the calorimetric gas cell 63 where a portion of its energy may be absorbed if an absorbing gas is present and the frequency of the first beam corresponds to a fundamental absorption peak of the absorbing gas(es). Upon emerging from the calorimetric gas cell 63, the first beam is disposed of in a beam dump 73.

A microphone 75 is positioned in the calorimetric gas cell 63 to detect any optoacoustic signals generated by absorption within the calorimetric gas cell 63. The microphone is coupled to the first electronic circuitry 67 which measures the amplitude of the optoacoustic signals. As previously discussed, the energy absorbed by the gas in the calorimetric gas cell 63 is proportional to the optoacoustic signal. The first electronic circuitry 67, which may be a computer with appropriate programming for handling the inputs described herein or any other proprietary electronic circuitry, uses the absorption measurement to control the wavelength selector 55 and select the angle of the wavelength selecting component 53, thus selecting an appropriate beam frequency. The beam frequency may be chosen to either correspond to a fundamental absorption frequency of the specified component or not correspond to a fundamental absorption frequency of the specified component, depending upon the step being executed in the method described in detail below. The first electronic circuitry 67 also normalizes the absorption measurement using the power of the first beam incident on the calorimetric gas cell 63 and outputs the normalized absorption measurement to the second electronic circuitry 77. The second electronic circuitry 77 is may be connected to a plurality of first electronic circuitry (and thus a plurality of apparatus similar to the one illustrated in FIG. 9) and uses previously determined calibration constants to convert the normalized absorption measurement into a concentration measurement of the specified component. Alternatively, where the second electronic circuitry 77 is connected to only a single first electronic circuitry 67, the two components may be combined into a single unit.

The apparatus illustrated in FIG. 9 measures the concentration of a specified component in human gas emissions by separately passing a beam at two discrete frequencies through the gas cell 63 at distinct and different times. The first beam frequency is near a fundamental absorption peak frequency of the specified component, such that by increasing the pressure in the gas cell 63, the nearby absorption peak may be broadened to at least partially encompass the first discrete frequency. The second discrete frequency is not near a fundamental absorption peak frequency of the specified component. Each beam frequency is selected by adjusting the angle of the wavelength selecting component 53, as controlled by the grating selector 67. Also, for each beam frequency the first electronics 67 normalizes the detected optoacoustic signal using the reference signal. The normalized signal at the first frequency is the absorption of the specified component and any other materials present that absorb at the first frequency, such as, for example, carbon dioxide, water vapor, or other unknown materials. The normalized signal at the second frequency is only the absorption of any other materials present which absorb at the second frequency. The second electronics 77 determines the concentration of the specified component using the difference between the normalized absorption signals obtained at the first and second frequencies.

Optionally, the beam may be passed through the calorimetric gas cell 63 at a third discrete frequency that is near a fundamental absorption peak frequency of the specified component that is different from the absorption peak the first discrete frequency is near, such that the increased pressure in the calorimetric gas cell 63 causes the nearby absorption peak to broaden and at least partially encompass the third discrete frequency. The reference signal and the optoacoustic signal in the calorimetric gas cell 63 are measured at the third discrete frequency, and the normalized signal is determined by the first electronic circuitry 67. The normalized signal at the third discrete frequency is the absorption of the specified component and any other materials present that absorb at the third frequency. The difference between the normalized absorption signals obtained at the second and third frequencies are used to verify the concentration obtained using the first discrete frequency. This confirmation helps ensure that there were no unknown absorbing contaminants in the gas cell which had an effect on the absorption measurement at the first frequency.

The elements of the apparatus illustrated in FIG. 9 may be chosen such that the overall measurement time of the apparatus, using all three beam frequencies, is less than ten seconds. For example, if a carbon dioxide laser, having an output power of approximately 2 W and a response time of less than approximately one second to change optical grating angles, is used as the laser 53 and the first and second electronic circuitry 67, 77 have sufficient computational speed, then measurement time of the apparatus would be less than ten seconds. Those skilled in the art will recognize that through the judicious selection of the proper equipment, the measurement time of the apparatus illustrated in FIG. 9 may be reduced to less than one second.

The following example describes the preferred method for obtaining a component concentration measurement of ammonia in human breath using the apparatus illustrated in FIG. 9. A human breath sample also contains approximately 4% carbon dioxide and water vapor at saturated levels corresponding to normal body temperatures, the presence of which will interfere with an absorption measurement of ammonia. However, the following method may be used to overcome the interference caused by the presence of such impurities.

The laser 51 is preferably a carbon dioxide laser which is tuned to a wavelength of approximately 9.3 μm using the optical grating 53 and the wavelength selector 55. This wavelength corresponds to the laser emitting a beam on the 9R30 transition of carbon dioxide and is near a fundamental absorption peak of ammonia gas but is not exactly coincident with it. The carbon dioxide and the water vapor present in the gas cell 63, however, also absorb energy at the 9R30 transition, thus creating background absorption to the ammonia absorption measurement. Of these two additional absorbers, absorption by carbon dioxide generates the greatest amount of background. To increase the absorption of ammonia at the 9R30 transition, the gas pressure in the gas cell is increased. The pressure within the gas cell is preferably 500 Torr and is chosen to maximize the absorption of ammonia and minimize the absorption of carbon dioxide at the 9R30 transition. The absorption peak of ammonia is broadened by increasing the gas pressure in the gas cell, thereby increasing the absorption of ammonia at the frequency corresponding to the 9R30 transition. Conversely, increasing the gas pressure in the gas cell 63 minimizes the absorption of carbon dioxide by broadening the carbon dioxide absorption feature, thereby reducing the peak absorption of carbon dioxide at the 9R30 transition.

Following the absorption measurement at the 9R30 transition, the laser 51 is tuned to another transition of carbon dioxide that is not near a fundamental absorption peak of ammonia, such as, for example, the 9R26 transition. Any carbon dioxide transition may be chosen which is not near a fundamental absorption peak of ammonia because any other transition line of the carbon dioxide laser will be absorbed by any carbon dioxide present in the gas emissions. The optoacoustic signal and reference signal are measured at the 9R26 transition and scaled to take into account the different, but calculable, absorption coefficients of carbon dioxide gas at the two different transitions. The net absorption, and thus the concentration, of ammonia is obtained by taking the difference in the normalized signals at the 9R30 and 9R26 transitions.

Finally, to assure that the net signal obtained from the 9R30 and 9R26 transitions corresponds only to ammonia absorption and not to some other unknown source, the laser is tuned to another transition that is near a fundamental absorption peak of ammonia and different from the absorption peak which the 9R30 transition is near, such as, for example, the 9R16 transition. The 9R16 transition may be used, even though the absorption of ammonia is approximately a factor of ten smaller than at the 9R30 transition, because the primary purpose of the absorption measurement at this transition is to confirm the concentration measurement obtained using the 9R30 transition. Using the measurement obtained at the 9R16 and 9R26 transitions, the net absorption is determined at the 9R16 transition. The concentration of the specified component thusly obtained using the 9R16 and 9R30 transitions may then be compared to ensure the absorption measurement at the 9R30 transition was not contaminated by the presence of an unknown absorbing material.

Figure 10:
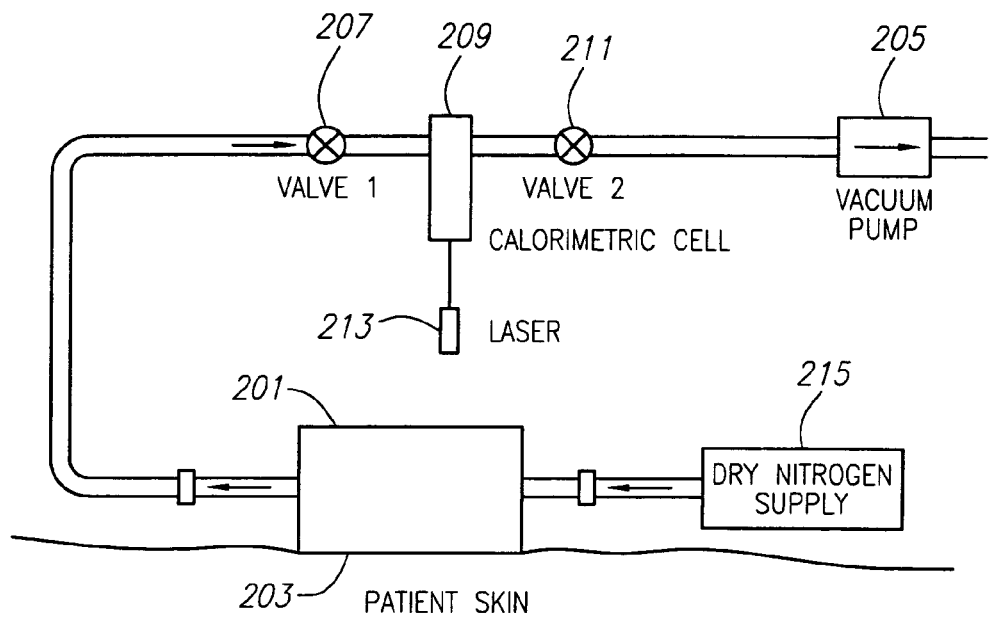
FIG. 10 illustrates a skin gas detector.
Figure 11:
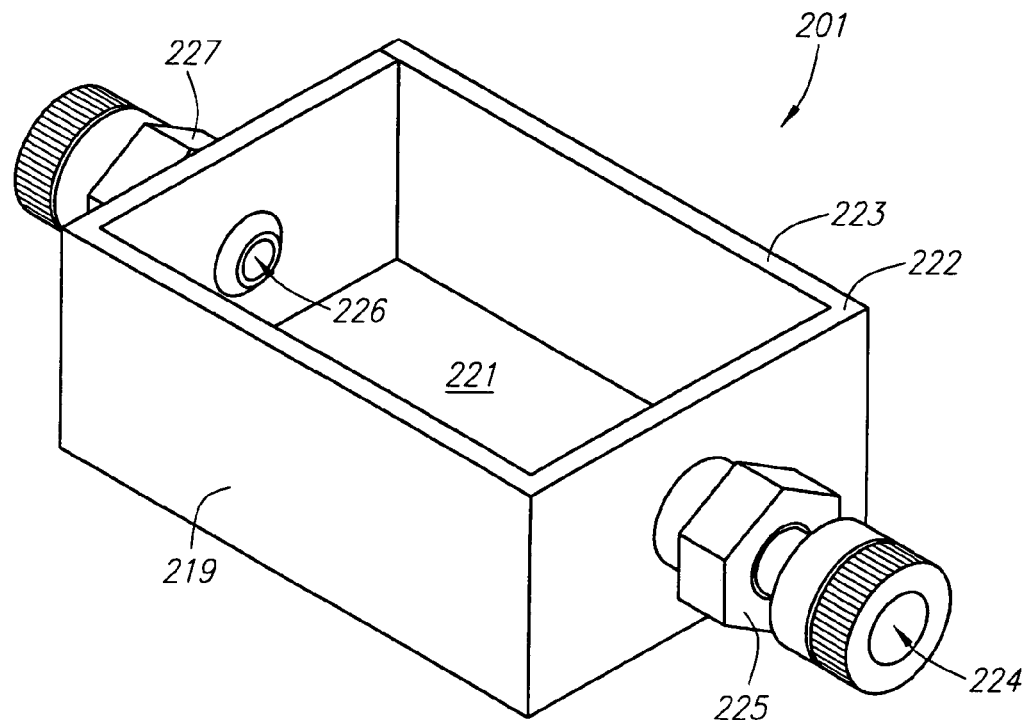
FIG. 11 is a perspective view of a collection chamber for the apparatus of FIG. 10.

FIGS. 10 and 11 illustrate an alternative embodiment in which gas emitted through human skin may be collected to measure the concentration of a specified component within the collected gas. As illustrated in FIG. 10, a skin gas collection chamber 201 is placed over a patient's skin 203 to collect the gases being emitted therefrom. An inert gas source 215 such as, for example, the dry nitrogen in FIG. 10, is pumped into the skin gas collection chamber 201. A vacuum pump 205 pumps the mixture of inert gas and emitted gas through a first valve 207 and into a calorimetric gas cell 209. A second valve 211 is disposed between the vacuum pump 205 and the gas cell 209. The first valve 207 and the second valve 211 may be used to adjust the pressure within the gas cell 209. A laser 213 passes a tunable optical radiation beam through the gas cell 209 to measure the concentration of a specified component in the emitted skin gas using any one of the methods previously described herein.

FIG. 11 is a detailed illustration of a skin gas collection chamber 201. The skin gas collection chamber 201 is preferably constructed using stainless steel, however any material may be used that is non-porous and non-reactive to the specified component being detected. The skin gas collection chamber 201 depicted in FIG. 11 is rectangular, however other shapes may also be used because the skin gas collection chamber 201 is not shape-dependant. The housing 219 of the skin gas collection chamber 201 define an interior space 221. The housing 219 defines a planar opening 223 on a first side of the skin gas collection chamber 201. The edges 222 of the planar opening 223 are preferably rounded and moderately polished to allow the formation of a good seal when the planar opening 223 is placed firmly against an exposed portion of a patient's skin. A good seal is preferred to prevent gases in the interior space 221 from escaping or allowing ambient gases into the interior space 221 during collection. Alternatively, a separate soft sealing material such as rubber or silicone may be added as a gasket around the planar opening 223 to form a more rigorous seal, or a band such as Velcro™ may be used to hold the skin gas collection chamber 201 in place. The skin gas collection chamber 201 further comprises an inlet 224 on a second side of the housing 219, through which inert gas may be pumped from the inert gas source 215 to the interior space 221, and an outlet 226 on a third side of the housing 219 through which the mixture of skin gases and inert gas may be pumped out of the interior space 221 for analysis. The inlet 224 preferably comprises an inlet connector 225 and the outlet 226 preferably comprises an outlet connector 227, each affixed to the housing 219. The inlet and outlet connectors 225, 227 preferably comprise quick connect/disconnect fittings such as, for example, Cajon™ brand connectors. In FIG. 10, flexible tubing or piping (not shown) is preferably used in conjunction with the inlet and outlet connectors 225, 227 to direct the flow of gas into and out of the interior space 221.

FIGS. 12A and 12B show test results employing the apparatus of FIG. 10 employed to detect ammonia emerging from a test subject's skin. The results shown in FIG. 12A were obtained by passing a beam at frequency $f_1$ through the gas cell, where $f_1$ corresponds to a fundamental absorption peak frequency of ammonia, and measuring the resulting optoacoustic signal. A first measurement was taken by exposing the skin gas collector to the ambient air and measuring the output signal of the detector. Second, the output signal was measured with the skin gas collector placed against the test subject's skin for two minutes. Third, the output signal was again measured after the skin gas collector was exposed to the ambient air for a period of five minutes. The range for the net signal is obtained by comparing the skin signal with the ambient air signals before and after the skin signal was taken. The net skin signal of FIG. 12A may be compared to the net skin signal of FIG. 12B. The results shown in FIG. 12B were obtained by passing a beam at frequency $f_2$ through the gas cell, where $f_2$ does not correspond to a fundamental absorption peak frequency of ammonia. The same measurements taken using the laser at frequency $f_1$ were taken using the laser at frequency $f_2$ and are displayed in FIG. 12B. The difference in the range of net skin signals displayed in FIGS. 12A and 12B is an indication that Ammonia is present in the gas emitted from the test subject's skin.

Figure 13:
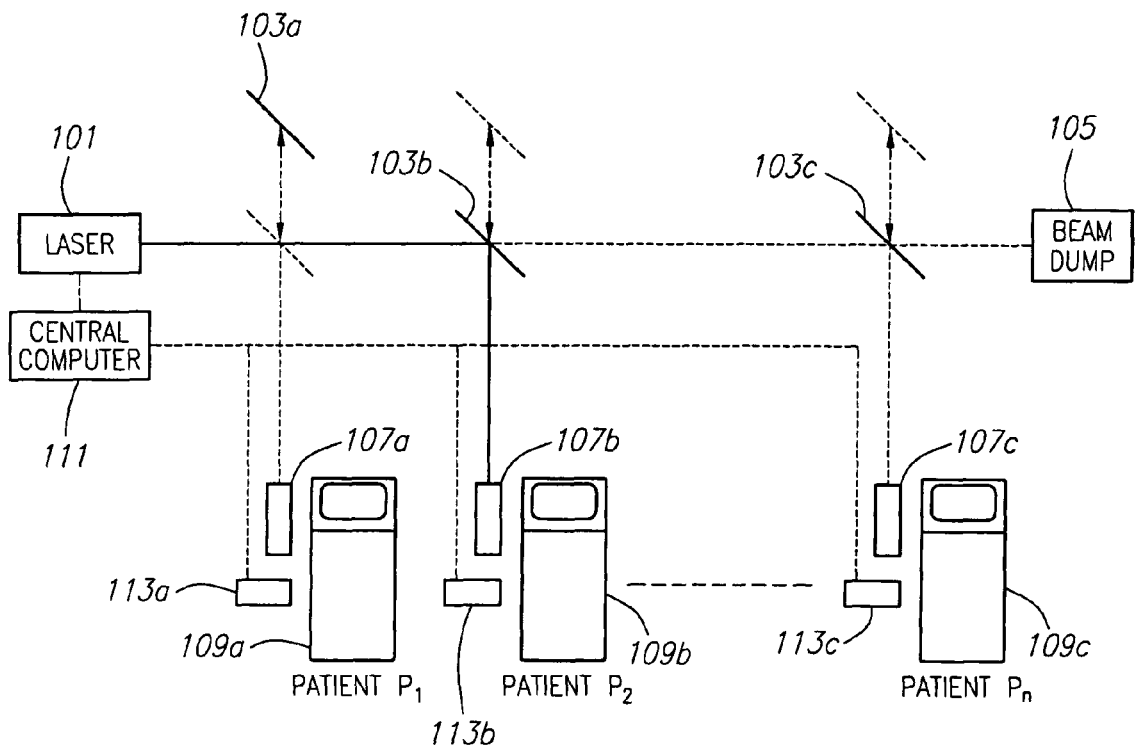
FIG. 13 illustrates a single tunable optical radiation beam multiplexed in switched mode.
Figure 14:
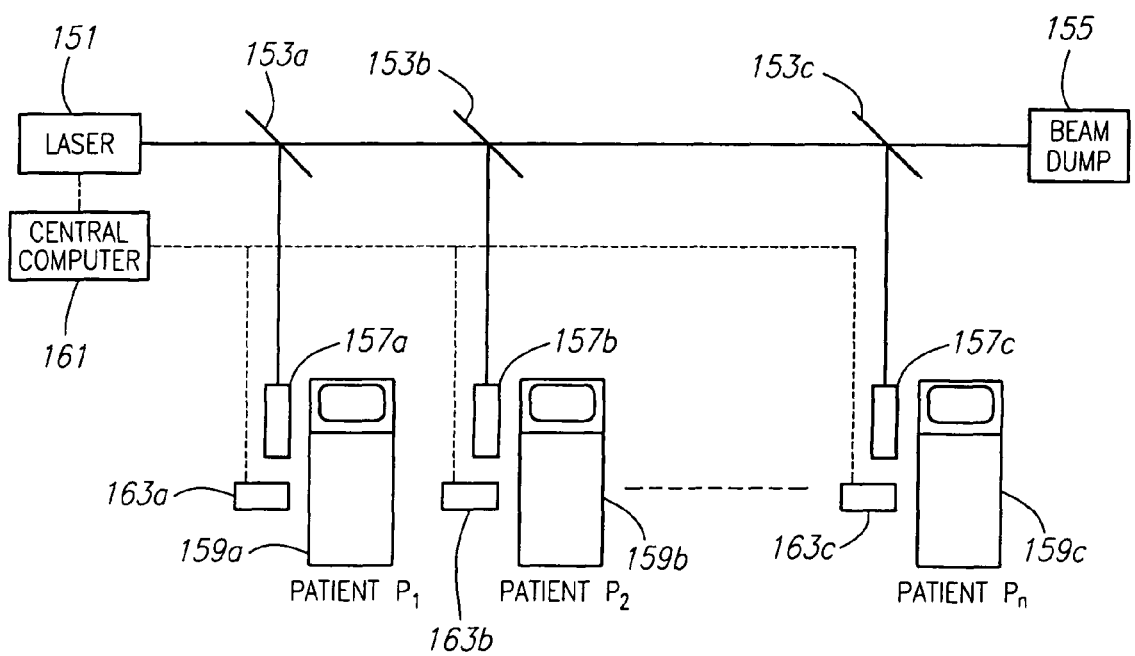
FIG. 14 illustrates a single tunable optical radiation beam multiplexed in unswitched mode.

As illustrated in FIGS. 13 and 14, any of the above embodiments may be enhanced by multiplexing the laser so that the beam may be directed to a plurality of medical systems, each system comprising a calorimetric cell or other medical equipment utilizing a laser. This multiplexing method comprises directing the beam through a beam guide (not shown) to a plurality of endpoints, wherein one of the plurality of medical systems is positioned at each endpoint. The beam guide preferably comprises sealed conduits, optical fibers or any other material or system that is known to those skilled in the art and capable of transporting a coherent beam of optical radiation.

The laser used in the multiplexing system may comprise a low- or high-power laser. If a low-power laser is used, such as the aforementioned semiconducting laser, the multiplexing method is preferably operated in a switched mode. The switched mode comprises directing a beam towards a plurality of medical systems, wherein the total number of medical systems that may utilize the beam is limited by the time each medical system requires use of the beam to perform a diagnosis. A high-power laser may be operated in the unswitched mode. In the unswitched mode, a single laser may simultaneously provide a beam to many different medical systems, wherein the total number of medical systems that may utilize the beam is limited by the incident power of the laser and the power requirements of each medical system.

FIG. 13 illustrates a multiplexed system being operated in the switched mode. The laser 101 directs a beam towards a plurality of sequentially positioned totally reflective mirrors 103a-c. Each mirror 103a-c has a first position and a second position and each is associated with a single medical system 107a-c, which for purposes of the following description is the optoacoustic gas cell illustrated in FIG. 4, with each gas cell 107a-c being used in the diagnosis of a patient 109a-c. The medical systems 107a-c may also comprise any apparatus disclosed herein or any other apparatus utilizing a laser for medical purposes.

The switched mode comprises directing a beam towards only one of the gas cells 107a-c at any give time. The gas cell 107b to which the beam is directed depends upon the positions of the mirrors 103a-c. When in the first position, a mirror is placed in the path of the beam. In the sequence of mirrors, the first mirror in the first position completely reflects the beam towards its associated gas cell, thereby preventing the beam from reaching all remaining mirrors in the sequence and their associated gas cells. When in the second position, the first mirror is completely removed from the path of the beam and allows the beam to pass to the next sequentially placed mirror. Thus, in FIG. 13, the first mirror 103a in the sequence, being in the second position, does not affect the beam, while the second mirror 103b in the sequence, now being the first mirror in the sequence in the first position, reflects the beam to its associated gas cell 107b. The beam does not pass through to the last mirror 103c in the sequence. Therefore, the patient 109b connected to the gas cell 107b will be diagnosed.

Once the diagnosis of one patient is complete, the beam may be redirected to a different gas cell by changing the position of one or more mirrors, thereby allowing a second patient to be diagnosed. The second patient may be connected to any cell along the path of the beam. Alternatively, if none of the mirrors 103a-c are in the first position, the beam is directed towards a beam dump 105 which harmlessly dissipates the beam's energy.

The laser 101, the mirrors 103a-c, and the gas cells 107a-c in FIG. 13 are preferably connected to a central computer 111 which organizes the work flow and performs such tasks including, but not limited to, tracking the utilization requirements of the gas cells 107a-c, tracking the gas cell 107a-c currently using the beam, scheduling utilization times for each gas cell 107a-c, thus determining when beam utilization may begin, tracking the positions of the mirrors 103a-c, actuating movement of the mirrors 103a-c between the first and second positions, determining when a gas cell 107a-c has completed a diagnosis and has finished utilizing the beam, detecting when a patient 109a-c has connected to or disconnected from a gas cell 107a-c, and detecting when the diagnosis of a patient 109a-c is completed and notifying the patient or other appropriate medical personnel of the completion.

In performing the above functions, the computer 111 preferably relies on input from the patient 109a-c or medical personnel. This input is obtained from control and monitoring stations 113a-c connected to the computer 111 and located nearby each gas cell 107a-c. These stations 113a-c preferably provide each patient 109a-c with information such as when to connect to the gas cell 107a-c and when to disconnect. The information is preferably provided through a series of LED's, which convey predefined instructions to the patient when lit, or through an LCD display to convey instructions.

FIG. 14 illustrates a multiplexed system operating in the unswitched mode. When operated in the unswitched mode, a more powerful tunable laser 151 is used because all of the cells 157a-c utilize the beam simultaneously. In this mode, the number of cells that may utilize the laser 151 is limited by the incident power of the laser because as previously stated, each cell requires approximately 1 W of incident power to achieve a detection resolution of approximately 1 ppB. Examples of more powerful lasers include but are not limited to the aforementioned CO2 laser, CO laser, spin-flip Raman laser, and quantum cascade semiconducting laser.

The unswitched mode comprises directing a beam at a series of beam splitters 153a-c, each beam splitter 153a-c reflecting approximately the power needed by a single gas cell to an associated gas cell 157a-c and transmitting the remainder to the next beam splitter 153a-c. Any power remaining in the beam after having passed through all the beam splitters 153a-c is directed towards a beam dump 155. In this manner, many patients 159a-c may be diagnosed simultaneously. A central computer 161 is also preferably employed in the unswitched mode for the same purposes a computer is used in the switched mode. Similar to the switched mode in FIG. 13, the central computer 161 is connected to control and monitoring stations 163a-c located nearby each cell 157a-c. These stations 163a-c operate in the same manner as they do in the switched mode described in relation to FIG. 13. Additionally, the switched and unswitched modes may be combined to increase the maximum number of medical systems that may utilize the beam from a single high-power laser.

In either the switched or unswitched modes, where the detection of multiple chemical species is required, a tunable laser with a wide tunable range may be employed. Under such circumstances, the laser continuously cycles through its available range for utilization in the medical systems. The computer system constantly records the time and the laser wavelength. A patient may connect to any available cell at any time, with the computer recording the time of connection and notifying the patient when the laser has cycled through all relevant wavelengths required for a complete diagnosis.

The above multiplexing modes may also be demand-driven. This method preferably employs the central computer for determining which patient or set of patients has the most immediate priority for diagnosis. The computer is preferably pre-programmed with information regarding the time requirements, wavelength, tuning range, and integration time for all medical diagnostic uses of the laser employed at any given facility. Taking into account the priority needs and all the pre-programmed information, the computer schedules beam usage, notifying each patient prior to providing the beam for a diagnosis, i.e. when a patient should breathe into the calorimetric cell, and when diagnosis is complete.

Thus a method for high sensitivity detection of component concentrations in human gas emissions has been disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

The invention claimed is:
1. A diagnostic method for high sensitivity detection of component concentrations in human gas emissions comprising:
(a) collecting a gas sample in a gas cell, wherein the gas sample may contain a specified component being asso- ciated with a plurality of fundamental absorption peak frequencies, and wherein the gas sample contains a plurality of other components;

(b) passing, at distinct and different times, a tunable optical radiation beam at a first frequency and at a second frequency through the gas cell (1) when the gas cell contains a reference sample having a known concentration of the specified component and (2) when the gas cell contains the gas sample, wherein the first frequency corresponds to one of the fundamental absorption peak frequencies and wherein the second frequency is used to measure any background absorptions caused by the plurality of other components;

(c) measuring, after each passing of the tunable optical radiation beam through the gas cell, an optoacoustic signal in the gas cell detected by an acoustic microphone and a power measurement of the tunable optical radiation beam; and (d) determining a concentration of the specified component in the gas sample using the optoacoustic signals and the power measurements obtained from the passing of the tunable optical radiation beam at the first frequency and at the second frequency through the gas cell.

2. The method of claim 1, wherein the gas sample is collected from expired human breath.

3. The method of claim 1, wherein the gas sample is collected from gas emissions from human skin.

4. The method of claim 3, wherein the step of collecting the gas sample further comprises:
   (a) sealing a collection chamber having a first side with a planar opening by placing the first side firmly against skin;
   (b) delivering into the collection chamber a steady flow of an inert gas; and
   (c) collecting the gas sample from the collection chamber into the gas cell.

5. The method of claim 1, wherein the specified component is ammonia.

6. The method of claim 1, wherein the specified component is nitric oxide.

7. The method of claim 1, wherein the specified component comprises a ketone.

8. The method of claim 1, wherein the specified component comprises an alcohol.

9. The method of claim 1, wherein the specified component comprises an alkane.

10. The method of claim 1, wherein said tunable optical radiation beam is multiplexed so that the beam may be passed through a plurality of gas cells.

11. The method of claim 10 further comprising detecting when a patient connects to one of the plurality of gas cells, said patient providing the gas sample.

12. The method of claim 10 further comprising notifying a patient when to connect to one of the plurality of gas cells, said patient providing the gas sample.

13. The method of claim 10 further comprising notifying a patient of a completed diagnosis after determining the concentration of the specified component, said patient providing the gas sample.

14. The method of claim 10 further comprising the tunable optical radiation beam being simultaneously passes through at least two of the plurality of gas cells.

15. A diagnostic method for high sensitivity detection of component concentrations in human gas emissions comprising:
   (a) collecting a gas sample in a calorimetric gas cell having an acoustic microphone within said calorimetric gas cell, wherein the gas sample may contain a specified component being associated with a plurality of fundamental absorption peak frequencies, and wherein the gas sample contains a plurality of other components;

(b) passing, at distinct and different times, a pulsed discretely tunable optical radiation beam at a first frequency and at a second frequency through the calorimetric gas cell (1) when the calorimetric gas cell contains a reference sample having a known concentration of the specified component and (2) when the calorimetric gas cell contains the gas sample, wherein the first frequency is near a first of the fundamental absorption peak frequencies, and wherein the second frequency is used to measure any background absorptions caused by the plurality of other components;

(c) adjusting the pressure in the calorimetric gas cell to increase an absorption of the specified component at the first frequency;

(d) measuring, after the tunable optical radiation beam passes through the calorimetric gas cell, as first signal outputs an optoacoustic signal in the calorimetric gas cell detected by the acoustic microphone when the tunable optical radiation beam passes through the gas cell at the first frequency, as second signal outputs a power of the tunable optical radiation beam at the first frequency, as third signal outputs an optoacoustic signal in the calorimetric gas cell detected by the acoustic microphone when the optical radiation beam passes through the gas cell at the second frequency, and as fourth signal outputs a power of the tunable optical radiation beam at the second frequency; and (e) determining a concentration of the specified component in the gas sample using the first, second, third, and fourth signal outputs obtained from the reference sample and the gas sample.

16. The method of claim 15, wherein:

step (b) further comprises passing the pulsed discretely tunable optical radiation beam at a third frequency through the calorimetric gas cell (1) when the calorimetric gas cell contains a reference sample having a known concentration of the specified component and (2) when the calorimetric gas cell contains the gas sample, wherein the third frequency is near a second of the fundamental absorption peak frequencies that is different from the first fundamental absorption peak frequency;

step (d) further comprises measuring, after the tunable optical radiation beam passes through the calorimetric gas cell, as fifth signal outputs an optoacoustic signal in the calorimetric gas cell detected by the acoustic microphone when the tunable optical radiation beam passes through the gas cell at the third frequency, and as sixth signal outputs a power of the tunable optical radiation beam at the third frequency; and step (d) further comprises verifying the concentration of the specified component in the gas sample using the third, fourth, fifth, and sixth signal outputs obtained from the reference sample and the gas sample.

17. The method of claim 1, wherein the gas cell is placed in an optical cavity.

* * * * *